(12) United States Patent
Chang (10) Patent No.: US 8,377,441 B2
(45) Date of Patent: Feb. 19, 2013

(54) TREATING BREAST CANCER WITH ANTI-IL-19 ANTIBODY

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 271 days.

(21) Appl. No.: 12/849,377

(22) Filed: Aug. 3, 2010

(65) Prior Publication Data

US 2012/0034208 A1 Feb. 9, 2012

(51) Int. Cl.
*A61K 39/395* (2006.01)

(52) U.S. Cl. ............... 424/133.1; 424/138.1; 424/141.1; 424/143.1; 424/145.1

(58) Field of Classification Search .......................... None
See application file for complete search history.

(56) References Cited

U.S. PATENT DOCUMENTS

| 5,693,762 | A | 12/1997 | Queen et al. | |
|---|---|---|---|---|
| 7,435,800 | B2 | 10/2008 | Chang | |
| 2004/0076606 | A1* | 4/2004 | Chang | 424/85.2 |
| 2005/0282233 | A1 | 12/2005 | Eriksson et al. | |
| 2009/0048432 | A1 | 2/2009 | Chang | |

OTHER PUBLICATIONS

Brown et al (J. Immunol. May 1996; 156(9):3285-3291.*
Vajdos et al (J. Mol. Biol. Jul. 5, 2002;320(2); 415-428).*
Jung et al., "Analysis of the expression profiles of cytokines and cytokine-related genes during the progression of breast cancer growth in mice", *Oncology Reports* 22: 1141-1147, 2009.
Liao et al., "IL-19 Induced Th2 Cytokines and Was Up-Regulated in Asthma Patients", *J. Immunol.* 2004; 173; 6712-6718.
Hsing et al., "The distribution of interleukin-19 in healthy and neoplastic tissue", *Cytokine* 44 (2008) 221-228.
Alanara et al., "Expression of IL-10 family cytokines in rheumatoid arthritis: elevated levels of IL-19 in the joints", *Scand J Rheumatol* 2010;39:118-126.
Sakurai et al., "Expression of IL-19 and its receptors in RA: potential role for synovial hyperplasia formation", *Rheumatology* 2008; 47:815-820.
Jordan et al., Human IL-19 regulates immunity through auto-induction of IL-19 and production of IL-10. Eur J Immunol. May 2005;35(5):1576-82.

* cited by examiner

*Primary Examiner* — Sheela J Huff
(74) *Attorney, Agent, or Firm* — Wolf, Greenfield & Sacks, P.C.

(57) ABSTRACT

Use of an anti-IL-19 antibody for treating breast cancer, either alone or in combination with an anti-IL-20 and/or anti-IL-20R1 antibody.

21 Claims, 3 Drawing Sheets

SEQUENCE LISTING

```
<160> NUMBER OF SEQ ID NOS: 16

<210> SEQ ID NO 1
<211> LENGTH: 459
<212> TYPE: PRT
<213> ORGANISM: Mus musculus

<400> SEQUENCE: 1

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Asp Tyr Ala Trp Asn Trp Ile Arg Gln Phe Pro Gly Asn Lys Leu
        50                  55                  60

Glu Trp Met Val Tyr Ile Thr Tyr Ser Gly Ile Thr Gly Tyr Asn Pro
65                  70                  75                  80

Ser Leu Lys Ser Arg Ile Ser Ile Thr Arg Asp Thr Ser Lys Asn Gln
                85                  90                  95
```

-continued

Phe Phe Leu Gln Leu Asn Ser Val Thr Thr Gly Asp Thr Ala Thr Tyr
            100                 105                 110

Tyr Cys Ala Arg Tyr Thr Thr Thr Ala Phe Asp Tyr Trp Gly Gln Gly
        115                 120                 125

Thr Thr Leu Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Val Thr Val Pro Ser Ser
        195                 200                 205

Thr Trp Pro Ser Glu Thr Val Thr Cys Asn Val Ala His Pro Ala Ser
    210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
                245                 250                 255

Pro Lys Pro Lys Asp Val Leu Thr Ile Thr Leu Thr Pro Lys Val Thr
            260                 265                 270

Cys Val Val Val Asp Ile Ser Lys Asp Asp Pro Glu Val Gln Phe Ser
        275                 280                 285

Trp Phe Val Asp Asp Val Glu Val His Thr Ala Gln Thr Gln Pro Arg
    290                 295                 300

Glu Glu Gln Phe Asn Ser Thr Phe Arg Ser Val Ser Glu Leu Pro Ile
305                 310                 315                 320

Met His Gln Asp Trp Leu Asn Gly Lys Glu Phe Lys Cys Arg Val Asn
                325                 330                 335

Ser Ala Ala Phe Pro Ala Pro Ile Glu Lys Thr Ile Ser Lys Thr Lys
            340                 345                 350

Gly Arg Pro Lys Ala Pro Gln Val Tyr Thr Ile Pro Pro Lys Glu
        355                 360                 365

Gln Met Ala Lys Asp Lys Val Ser Leu Thr Cys Met Ile Thr Asp Phe
    370                 375                 380

Phe Pro Glu Asp Ile Thr Val Glu Trp Gln Trp Asn Gly Gln Pro Ala
385                 390                 395                 400

Glu Asn Tyr Lys Asn Thr Gln Pro Ile Met Asp Thr Asp Gly Ser Tyr
                405                 410                 415

Phe Val Tyr Ser Lys Leu Asn Val Gln Lys Ser Asn Trp Glu Ala Gly
            420                 425                 430

Asn Thr Phe Thr Cys Ser Val Leu His Glu Gly Leu His Asn His His
        435                 440                 445

Thr Glu Lys Ser Leu Ser His Ser Pro Gly Lys
    450                 455

<210> SEQ ID NO 2
<211> LENGTH: 117
<212> TYPE: PRT
<213> ORGANISM: Artificial sequence
<220> FEATURE:
<223> OTHER INFORMATION: Synthetic peptide

<400> SEQUENCE: 2

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Val Tyr Ile Thr Tyr Ser Gly Ile Thr Gly Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ala Thr Tyr Tyr Cys
                85                  90                  95

Ala Arg Tyr Thr Thr Thr Ala Phe Asp Tyr Trp Gly Gln Gly Thr Thr
            100                 105                 110

Leu Thr Val Ser Ser
        115
```

```
<210> SEQ ID NO 3
<211> LENGTH: 1380
<212> TYPE: DNA
<213> ORGANISM: Mus musculus

<400> SEQUENCE: 3
atgagagtgc tgattctttt gtggctgttc acagcctttc ctggtatcct gtctgatgtg     60
cagcttcagg agtcgggacc tggcctggtg aaaccttctc agtctctgtc cctcacctgc    120
actgtcactg gctactcaat caccagtgat tatgcctgga actggatccg gcagtttcca    180
ggaaacaaac tggagtggat ggtctacata acctacagtg gtatcactgg ctataacccc    240
tctctcaaaa gtcggatctc tatcactcga gacacatcca agaaccagtt cttcctgcag    300
ttgaattctg tgactactgg ggacacagcc acctattact gtgcaagata tactacgact    360
gcgtttgact actggggcca aggcaccact ctcacggtct cctcagccaa aacgacaccc    420
ccatctgtct atccactggc ccctggatct gctgcccaaa ctaactccat ggtgaccctg    480
ggatgcctgg tcaagggcta tttccctgag ccagtgacag tgacctggaa ctctggatcc    540
ctgtccagcg gtgtgcacac cttcccagct gtcctgcagt ctgacctcta cactctgagc    600
agctcagtga ctgtcccctc agcacctggg cccagcgaga ccgtcacctg caacgttgcc    660
cacccggcca gcagcaccaa ggtggacaag aaaattgtgc ccagggattg tggttgtaag    720
ccttgcatat gtacagtccc agaagtatca tctgtcttca tcttccccccc aaagcccaag    780
gatgtgctca ccattactct gactcctaag gtcacgtgtg ttgtggtaga catcagcaag    840
gatgatcccg aggtccagtt cagctggttt gtagatgatg tggaggtgca cacagctcag    900
acgcaacccc gggaggagca gttcaacagc actttccgct cagtcagtga acttcccatc    960
atgcaccagg actggctcaa tggcaaggag ttcaaatgca gggtcaacag tgcagctttc   1020
cctgccccca tcgagaaaac catctccaaa accaaaggca gaccgaaggc tccacaggtg   1080
tacaccattc cacctcccaa ggagcagatg gccaaggata agtcagtctg acctgcatg    1140
ataacagact tcttccctga agacattact gtggagtggc agtggaatgg gcagccagcg   1200
gagaactaca agaacactca gcccatcatg gacacagatg gctcttactt cgtctacagc   1260
aagctcaatg tgcagaagag caactgggag gcaggaaata ctttcacctg ctctgtgtta   1320
catgagggcc tgcacaacca ccatactgag aagagcctct cccactctcc tggtaaatga   1380

<210> SEQ ID NO 4
```

```
<211> LENGTH: 351
<212> TYPE: DNA
<213> ORGANISM: Artificial sequence
<220> FEATURE:
<223> OTHER INFORMATION: synthetic oligo

<400> SEQUENCE: 4
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggatggtc tacataacct acagtggtat cactggctat     180
aacccctctc tcaaaagtcg gatctctatc actcgagaca catccaagaa ccagttcttc     240
ctgcagttga attctgtgac tactggggac acagccacct attactgtgc aagatatact     300
acgactgcgt ttgactactg gggccaaggc accactctca cggtctcctc a              351

<210> SEQ ID NO 5
<211> LENGTH: 238
<212> TYPE: PRT
<213> ORGANISM: Mus musculus

<400> SEQUENCE: 5

Met Lys Leu Pro Val Arg Leu Leu Val Leu Met Phe Trp Ile Pro Ala
1               5                   10                  15

Ser Arg Ser Asp Ile Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Lys Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 6
<211> LENGTH: 100
<212> TYPE: PRT
<213> ORGANISM: Artificial sequence
<220> FEATURE:
<223> OTHER INFORMATION: Synthetic peptide
```

<400> SEQUENCE: 6

| Asp | Ile | Val | Met | Thr | Gln | Thr | Pro | Leu | Ser | Leu | Pro | Val | Ser | Leu | Gly |
| 1 | | | | 5 | | | | | 10 | | | | | 15 | |

| Asp | Gln | Ala | Ser | Ile | Ser | Cys | Arg | Ser | Ser | Gln | Ser | Leu | Val | His | Ser |
| | | | 20 | | | | | 25 | | | | | 30 | | |

| Asn | Gly | Lys | Thr | Tyr | Leu | His | Trp | Tyr | Leu | Gln | Lys | Pro | Gly | Gln | Ser |
| | | 35 | | | | | 40 | | | | | 45 | | | |

| Pro | Lys | Leu | Leu | Ile | Tyr | Lys | Val | Ser | Asn | Arg | Phe | Ser | Gly | Val | Pro |
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |

| Ser | Arg | Val | Glu | Ala | Glu | Asp | Leu | Gly | Val | Tyr | Phe | Cys | Ser | Gln | Ser |
| | | | | 85 | | | | | 90 | | | | | 95 | |

| Thr | His | Val | Pro |
| | | | 100 |

<210> SEQ ID NO 7
<211> LENGTH: 717
<212> TYPE: DNA
<213> ORGANISM: Mus musculus

<400> SEQUENCE: 7

```
atgaagttgc ctgttaggct gttggtgctg atgttctgga ttcctgcttc caggagtgat      60
attgtgatga cccaaactcc actctccctg cctgtcagtc ttggagatca agcctccatc     120
tcttgcagat ctagtcagag ccttgtacac agtaatggaa aaacctattt acattggtac     180
ctgcagaagc caggccagtc tcctaagctc ctgatctaca agtttccaa ccgattttct      240
ggggtcccag acaggttcag tggcagtgga tcagggacag atttcacact caagatcagc     300
agagtggagg ctgaggatct gggagtttat ttctgctctc aaagcacaca tgttccgtgg     360
acgttcggtg gaggcaccaa gctggaaatc aaacggctg atgctgcacc aactgtatcc      420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat aacgacata cagctatac ctgtgaggcc       660
actcacaaga catcaacttc acccattgtc aagagcttca caggaatga gtgttag         717
```

<210> SEQ ID NO 8
<211> LENGTH: 300
<212> TYPE: DNA
<213> ORGANISM: Artificial sequence
<220> FEATURE:
<223> OTHER INFORMATION: Synthetic oligo

<400> SEQUENCE: 8

```
gatattgtga tgacccaaac tccactctcc ctgcctgtca gtcttggaga tcaagcctcc      60
atctcttgca gatctagtca gagccttgta cacagtaatg gaaaaaccta tttacattgg     120
tacctgcaga agccaggcca gtctcctaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagcac acatgttccg     300
```

<210> SEQ ID NO 9
<211> LENGTH: 1395
<212> TYPE: DNA

<213> ORGANISM: Mus musculus

<400> SEQUENCE: 9

| | | | | | |
|---|---|---|---|---|---|
| atgtacttgg | gactgaacta | tgtattcata | gtttttctct | taaatggtgt | ccagagtgaa | 60 |
| ttgaagcttg | aggagtctgg | aggaggcttg | gtgcagcctg | gaggatccat | gaaactctct | 120 |
| tgtgctgcct | ctggattcac | ttttagtgac | gcctggatgg | actgggtccg | ccagtctcca | 180 |
| gagaaggggc | ttgagtggat | tgctgaaatt | agaagcaaag | ctaataatta | tgcaacatac | 240 |
| tttgctgagt | ctgtgaaagg | gaggttcacc | atctcaagag | atgattccaa | aagtggtgtc | 300 |
| tacctgcaaa | tgaacaactt | aagagctgag | gacactggca | tttatttctg | taccaagtta | 360 |
| tcactacgtt | actggttctt | cgatgtctgg | ggcgcaggga | ccacggtcac | cgtctcctca | 420 |
| gccaaaacga | cacccccatc | tgtctatcca | ctggcccctg | gatctgctgc | ccaaactaac | 480 |
| tccatggtga | ccctgggatg | cctggtcaag | ggctatttcc | ctgagccagt | gacagtgacc | 540 |
| tggaactctg | gatccctgtc | cagcggtgtg | cacaccttcc | cagctgtcct | gcagtctgac | 600 |
| ctctacactc | tgagcagctc | agtgactgtc | ccctccagca | cctggcccag | cgagaccgtc | 660 |
| acctgcaacg | ttgcccaccc | ggccagcagc | accaaggtgg | acaagaaaat | tgtgcccagg | 720 |
| gattgtggtt | gtaagccttg | catatgtaca | gtcccagaag | tatcatctgt | cttcatcttc | 780 |
| cccccaaagc | ccaaggatgt | gctcaccatt | actctgactc | ctaaggtcac | gtgtgttgtg | 840 |
| gtagacatca | gcaaggatga | tcccgaggtc | cagttcagct | ggtttgtaga | tgatgtggag | 900 |
| gtgcacacag | ctcagacgca | accccgggag | gagcagttca | acagcacttt | ccgctcagtc | 960 |
| agtgaacttc | ccatcatgca | ccaggactgg | ctcaatggca | aggagttcaa | atgcagggtc | 1020 |
| aacagtgcag | ctttccctgc | ccccatcgag | aaaaccatct | ccaaaaccaa | aggcagaccg | 1080 |
| aaggctccac | aggtgtacac | cattccacct | cccaaggagc | agatggccaa | ggataaagtc | 1140 |
| agtctgacct | gcatgataac | agacttcttc | cctgaagaca | ttactgtgga | gtggcagtgg | 1200 |
| aatgggcagc | cagcggagaa | ctacaagaac | actcagccca | tcatggacac | agatggctct | 1260 |
| tacttcgtct | acagcaagct | caatgtgcag | aagagcaact | gggaggcagg | aaatactttc | 1320 |
| acctgctctg | tgttacatga | gggcctgcac | aaccaccata | ctgagaagag | cctctcccac | 1380 |
| tctcctggta | aatga | | | | | 1395 |

<210> SEQ ID NO 10
<211> LENGTH: 464
<212> TYPE: PRT
<213> ORGANISM: Mus musculus

<400> SEQUENCE: 10

Met Tyr Leu Gly Leu Asn Tyr Val Phe Ile Val Phe Leu Leu Asn Gly
1               5                   10                  15

Val Gln Ser Glu Leu Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Ser Gly Val Tyr Leu Gln Met Asn Asn Leu Arg Ala Glu Asp Thr
            100                 105                 110

Gly Ile Tyr Phe Cys Thr Lys Leu Ser Leu Arg Tyr Trp Phe Phe Asp
            115                 120                 125

Val Trp Gly Ala Gly Thr Thr Val Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 11
<211> LENGTH: 363
<212> TYPE: DNA
<213> ORGANISM: Artificial sequence
<220> FEATURE:
<223> OTHER INFORMATION: Synthetic oligo

<400> SEQUENCE: 11
gaattgaagc ttgaggagtc tggaggaggc ttggtgcagc ctggaggatc catgaaactc      60
tcttgtgctg cctctggatt cactttagt gacgcctgga tggactgggt ccgccagtct    120

```
ccagagaagg ggcttgagtg gattgctgaa attagaagca aagctaataa ttatgcaaca    180
tactttgctg agtctgtgaa agggaggttc accatctcaa gagatgattc caaaagtggt    240
gtctacctgc aaatgaacaa cttaagagct gaggacactg cattatttt ctgtaccaag    300 ttatcactac gttactggtt cttcgatgtc tggggcgcag ggaccacggt caccgtctcc    360
tca                                                                  363
```

```
<210> SEQ ID NO 12
<211> LENGTH: 121
<212> TYPE: PRT
<213> ORGANISM: Artificial sequence
<220> FEATURE:
<223> OTHER INFORMATION: Synthetic peptide

<400> SEQUENCE: 12

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
            100                 105                 110

Ala Gly Thr Thr Val Thr Val Ser Ser
        115                 120
```

```
<210> SEQ ID NO 13
<211> LENGTH: 720
<212> TYPE: DNA
<213> ORGANISM: Mus musculus

<400> SEQUENCE: 13
atgatgagtc ctgcccagtt cctgtttctg ttagtgctct ggattcggga aaccaacggt     60
gattttgtga tgacccagac tccactcact ttgtcggtta ccattggaca accagcctcc    120
atctcttgca agtcaagtca gagcctcttg gatagtgatg aaagacata tttgaattgg    180 ttgttacaga ggccaggcca gtctccaaag cacctcatct atctggtgtc taaactggac    240
tctggagtcc ctgacaggtt cactggcagt ggatcaggga ccgatttcac actgagaatc    300
agcagagtgg aggctgagga tttgggagtt tattattgct ggcaaagtac acattttccg    360
tggacgttcg gtggaggcac caagctggaa atcaaacggg ctgatgctgc accaactgta    420
tccatcttcc caccatccag tgagcagtta acatctggag gtgcctcagt cgtgtgcttc    480
ttgaacaact tctacaagtg gaagattgat ggcagtgaac gacaaaatgg cgtcctgaac    540
agttggactg atcagcccaa agacatcaat gtcgacagca agacagcac ctacagcatg    600 agcagcaccc tcacgttgac caaggacgag tatgaacgac ataacagcta cctgtgtgag    660
gccactcaca gacatcaac ttcacccatt gtcaagagct caacaggaa tgagtgttag     720
```

```
<210> SEQ ID NO 14
<211> LENGTH: 239
```

<212> TYPE: PRT
<213> ORGANISM: Mus musculus

<400> SEQUENCE: 14

```
Met Met Ser Pro Ala Gln Phe Leu Phe Leu Leu Val Leu Trp Ile Arg
1               5                   10                  15

Glu Thr Asn Gly Asp Phe Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
        50                  55                  60

Pro Gly Gln Ser Pro Lys His Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Arg Ile Ser Arg Val Glu Ala Glu Asp Leu Gly Val Tyr Tyr
                100                 105                 110

Cys Trp Gln Ser Thr His Phe Pro Trp Thr Phe Gly Gly Gly Thr Lys
            115                 120                 125

Leu Glu Ile Lys Arg Ala Asp Ala Ala Pro Thr Val Ser Ile Phe Pro
        130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
                180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235
```

<210> SEQ ID NO 15
<211> LENGTH: 339
<212> TYPE: DNA
<213> ORGANISM: Artificial sequence
<220> FEATURE:
<223> OTHER INFORMATION: Synthetic oligo

<400> SEQUENCE: 15

```
gattttgtga tgacccagac tccactcact ttgtcggtta ccattggaca accagcctcc    60
atctcttgca agtcaagtca gagcctcttg gatagtgatg gaaagacata tttgaattgg   120
ttgttacaga ggccaggcca gtctccaaag caccctcatct atctggtgtc taaactggac   180
tctggagtcc ctgacaggtt cactggcagt ggatcaggga ccgatttcac actgagaatc   240
agcagagtgg aggctgagga tttgggagtt tattattgct ggcaaagtac acattttccg   300
tggacgttcg gtggaggcac caagctggaa atcaaacgg                          339
```

<210> SEQ ID NO 16
<211> LENGTH: 113
<212> TYPE: PRT
<213> ORGANISM: Artificial sequence
<220> FEATURE:
<223> OTHER INFORMATION: Synthetic peptide

```
<400> SEQUENCE: 16

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65              70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

Arg
```

TREATING BREAST CANCER WITH ANTI-IL-19 ANTIBODY

BACKGROUND OF THE INVENTION

Breast cancer, e.g., ductal carcimona and lobular carcinoma, is the most common cancer in women worldwide. It affects one in eight women during their lives.

Treatments for breast cancer include chemotherapy, radiotherapy, and surgery. While satisfactory therapeutic efficacy has been observed in treating early-stage breast cancer, the 5-year survival rate for breast cancer patients in late stage is below 50%.

It is of great importance to develop new breast cancer therapy with high efficacy for all disease stages.

SUMMARY OF THE INVENTION

The present invention is based on unexpected discoveries that monoclonal antibody 1BB1, specific to human IL-19, effectively inhibits breast cancer cell proliferation and breast tumor growth, and prolongs survival of mice bearing breast cancer.

Accordingly, one aspect of this invention features a method of treating breast cancer with an effective amount of an anti-IL-19 antibody, either alone or in combination with an anti-IL-20 or anti-IL-20R1 antibody. The term "treating" as used herein refers to the application or administration of a composition including one or more active agents to a subject, who has breast cancer, a symptom of the breast cancer, or a predisposition toward breast cancer, with the purpose to cure, heal, alleviate, relieve, alter, remedy, ameliorate, improve, or affect the cancer, the symptoms of the cancer, or the predisposition toward the cancer. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The anti-IL-19, anti-IL-20, or anti-IL-20R1 antibody to be used in the method of this invention can be a naturally-occurring antibody (e.g., a monoclonal antibody), an antigen-binding fragment thereof (e.g., $F(ab')_2$, Fab, or Fv), or a genetically engineered antibody (e.g., chimeric antibody, humanized antibody, or single-chain antibody) that neutralizes IL-19, IL-20, or IL-20R1, i.e., binding to either antigen and blocking the signaling pathway mediated by it.

The anti-IL-19 antibody can contain (1) a heavy chain variable region ($V_H$) that includes all of the complementarity-determining regions (CDRs) in the $V_H$ of antibody 1BB1 (SEQ ID NO:2), and (2) a light chain variable region ($V_L$) that includes all of the CDRs in the $V_L$ of antibody 1BB1 (SEQ ID NO:6). In one example, this anti-IL-19 antibody contains the same $V_H$ and $V_L$ of 1BB1.

The anti-IL-20 antibody can contain (1) a $V_H$ that includes all of the CDRs in the $V_H$ of antibody 7E (SEQ ID NO:12), and (2) a $V_L$ that includes all of the CDRs in the $V_L$ of antibody 7E (SEQ ID NO:16). In one example, this anti-IL-20 antibody contains the same $V_H$ and $V_L$ of antibody 7E.

When the above-described composition contains two antibodies (i.e., an anti-IL-19 antibody and an anti-IL-20 or anti-IL-20R1 antibody), these two antibodies can form a bi-specific complex. In one example, both of the antibodies are Fab fragments that form a bi-specific antibody.

Also within the scope of this invention are (1) a pharmaceutical composition for breast cancer treatment, the composition containing an anti-IL-19 antibody and, optionally, an anti-IL-20 or anti-IL-20R1 antibody, and (2) the use of this composition in manufacturing a medicament for treating breast cancer.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Described herein is a method of treating breast cancer in a subject in need of the treatment (e.g., a human patient suffering from or at risk for breast cancer) with an anti-IL-19 antibody, either alone or in combination with an anti-IL-20 or anti-IL-20R1 antibody. As used herein, the term "antibody" refers to naturally-occurring immunoglobulins, antigen-binding fragments thereof, or generically engineered antibodies known in the art.

Naturally-occurring anti-IL-19, anti-IL-20 and anti-IL-20R1 antibodies, either polyclonal or monoclonal, can be prepared by conventional methods, using an IL-19 protein, an IL-20 protein, an IL-20R1 protein, or a fragment thereof as the inducing antigen. See, e.g., Harlow and Lane, (1988) Antibodies: A Laboratory Manual, Cold Spring Harbor Laboratory, New York. A "monoclonal antibody" refers to a homogenous antibody population and a "polyclonal antibody" refers to a heterogenous antibody population. These two terms do not limit the source of an antibody or the manner in which it is made.

Both IL-19 and IL-20 are cytokines well known in the art and IL-20R1 is a receptor of IL-20. Human IL-19, IL-20, and IL-20R1 can be retrieved from the GenBank under accession numbers:

Human IL-19 isoform 1: NP_715639 (protein) and NM_153758.1 (gene)

Human IL-19 isoform 2: NP_037503 (protein) and NM_013371.2 (gene)

Human IL-20: NP_061194 (protein) and NM_018724 (gene).

Human IL-20R1: NP_055247 (protein) and NM_014432.2 (mRNA)

To produce an anti-IL-19, anti-IL-20, or anti-IL-20R1 antibody, the protein or a fragment thereof can be coupled to a carrier protein, such as KLH, mixed with an adjuvant, and injected into a host animal. Antibodies produced in the animal can then be purified by a protein A column and/or affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and Corynebacterium parvum.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production. After obtaining antibodies specific to IL-19 or IL-20, their ability to neutralize IL-19 or IL-20 can be determined by a routine procedure.

Fully human anti-IL-19, anti-IL-20, and anti-IL-20R1 antibodies, such as those expressed in transgenic animals, are also features of the invention. See, e.g., Green et al., Nature Genetics 7:13 (1994), and U.S. Pat. Nos. 5,545,806, and 5,569,825.

Antigen-binding fragments (e.g., F(ab')$_2$, Fab, or Fv) of a naturally-occurring antibody can be generated by known techniques. For example, F(ab')$_2$ fragments can be produced by pepsin digestion of an antibody molecule and Fab fragments can be generated by reducing the disulfide bridges of F(ab')$_2$ fragments.

All of the anti-IL-19, anti-IL-20, and anti-IL-20R1 antibodies to be used in this invention can also be a genetically engineered antibody, e.g., a humanized antibody, a chimeric antibody, a single chain antibody (scFv), or a domain antibody (dAb; see Ward, et. Al., 1989, Nature, 341:544-546). Such an antibody has substantially the same antigen-binding residues/regions as a naturally-occurring antibody from which it derives, thereby preserving the same antigen specificity as the naturally-occurring antibody.

A humanized antibody contains a human immunoglobulin (i.e., recipient antibody) in which regions/residues responsible for antigen binding (i.e., the CDRs, particularly the specific-determining residues therein) are replaced with those from a non-human immunoglobulin (i.e., donor antibody). In some instances, one or more residues inside a frame region of the recipient antibody are also replaced with those from the donor antibody. A humanized antibody may also contain residues from neither the recipient antibody nor the donor antibody. These residues are included to further refine and optimize antibody performance. Antibodies can also be humanized by methods known in the art, e.g., recombinant technology.

A chimeric antibody is a molecule in which different portions are derived from different animal species, such as those having a variable region derived from a murine monoclonal antibody and a human immunoglobulin constant region. Such an antibody can be prepared via routine techniques described in, e.g., Morrison et al. (1984) Proc. Natl. Acad. Sci. USA 81, 6851; Neuberger et al. (1984) Nature 312, 604; and Takeda et al. (1984) Nature 314:452.

A single-chain antibody can be prepared via recombinant technology by linking a nucleotide sequence coding for a $V_H$ chain and a nucleotide sequence coding for a $V_L$ chain. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-19 can be identified from the library following routine procedures. Positive clones can be subjected to further screening to identify those that suppress IL-19 or IL-20 activity.

In one example, the anti-IL-19 antibody to be used in the method of this invention is monoclonal antibody 1BB1 (see Hsing et al., *Cytokine* 44:221-228; 2008), an antigen binding fragment thereof, or a genetically-engineered functional variant thereof. Shown below are the amino acid sequences for the heavy and light chains of this monoclonal antibody, as well as their encoding nucleotide sequences:

```
Heavy chain amino acid sequence:
                                                        (SEQ ID NO: 1)
M R V L I L L W L F T A F P G I L S D V Q L Q E S G P G L V K P S Q S L S L T

C T V T G Y S I T S D Y A W N W I R Q F P G N K L E W M V Y I T Y S G I T G Y

N P S L K S R I S I T R D T S K N Q F F L Q L N S V T T G D T A T Y Y C A R Y

T T T A F D Y W G Q G T T L T V S S A K T T P P S V Y P L A P G S A A Q T N S

M V T L G C L V K G Y F P E P V T V T W N S G S L S S G V H T F P A V L Q S D

L Y T L S S S V T V P S S T W P S E T V T C N V A H P A S S T K V D K K I V P

R D C G C K P C I C T V P E V S S V F I F P P K P K D V L T I T L T P K V T C

V V V D I S K D D P E V Q F S W F V D D V E V H T A Q T Q P R E E Q F N S T F

R S V S E L P I M H Q D W L N G K E F K C R V N S A A F P A P I E K T I S K T

K G R P K A P Q V Y T I P P P K E Q M A K D K V S L T C M I T D F F P E D I T
```

```
VEWQWNGQPAENYKNTQPIMDTDGSYFVYSKLNVQKSNW

EAGNTFTCSVLHEGLHNHHTEKSLSHSPGK
```
Italic region: signal peptide
Bold-faced region: variable chain (SEQ ID NO: 2)
Bold-faced and underlined regions: CDRs
Regular font regions: constant regions
Underlined region: hinge region Heavy chain nucleotide sequence:
(SEQ ID NO: 3)

*ATGAGAGTGCTGATTCTTTTGTGGCTGTTCACAGCCTTTCCTGGTATCCTGTCT*GATGTGCAGCTTCAGGAGTCGGGA

CCTGGCCTGGTGAAACCTTCTCAGTCTCTGTCCCTCACCTGCACTGTCACTGGCTACTCAATCACC<u>AGTGATTATGCC</u>

<u>TGG</u>AACTGGATCCGGCAGTTTCCAGGAAACAAACTGGAGTGGATGGTC<u>TACATAACCTACAGTGGTATCACTGGCTAT</u>

<u>AACCCCTCTCTCAAAAGT</u>CGGATCTCTATCACTCGAGACACATCCAAGAACCAGTTCTTCCTGCAGTTGAATTCTGTG

ACTACTGGGGACACAGCCACCTATTACTGTGCAAGA<u>TATACTACGACTGCGTTTGACTAC</u>TGGGGCCAAGGCACCACT

CTCACGGTCTCCTCAGCCAAAACGACACCCCCATCTGTCTATCCACTGGCCCCTGGATCTGCTGCCCAAACTAACTCC

ATGGTGACCCTGGGATGCCTGGTCAAGGGCTATTTCCCTGAGCCAGTGACAGTGACCTGGAACTCTGGATCCCTGTCC

AGCGGTGTGCACACCTTCCCAGCTGTCCTGCAGTCTGACCTCTACACTCTGAGCAGCTCAGTGACTGTCCCCTCCAGC

ACCTGGCCCAGCGAGACCGTCACCTGCAACGTTGCCCACCCGGCCAGCAGCACCAAGGTGGACAAGAAAATT<u>GTGCCC</u>

<u>AGGGATTGTGGTTGTAAGCCTTGCATATGTAC</u>AGTCCCAGAAGTATCATCTGTCTTCATCTTCCCCCCAAAGCCCAAG

GATGTGCTCACCATTACTCTGACTCCTAAGGTCACGTGTGTTGTGGTAGACATCAGCAAGGATGATCCCGAGGTCCAG

TTCAGCTGGTTTGTAGATGATGTGGAGGTGCACACAGCTCAGACGCAACCCCGGGAGGAGCAGTTCAACAGCACTTTC

CGCTCAGTCAGTGAACTTCCCATCATGCACCAGGACTGGCTCAATGGCAAGGAGTTCAAATGCAGGGTCAACAGTGCA

GCTTTCCCTGCCCCCATCGAGAAAACCATCTCCAAAACCAAAGGCAGACCGAAGGCTCCACAGGTGTACACCATTCCA

CCTCCCAAGGAGCAGATGGCCAAGGATAAAGTCAGTCTGACCTGCATGATAACAGACTTCTTCCCTGAAGACATTACT

GTGGAGTGGCAGTGGAATGGGCAGCCAGCGGAGAACTACAAGAACACTCAGCCCATCATGGACACAGATGGCTCTTAC

TTCGTCTACAGCAAGCTCAATGTGCAGAAGAGCAACTGGGAGGCAGGAAATACTTTCACCTGCTCTGTGTTACATGAG

GGCCTGCACAACCACCATACTGAGAAGAGCCTCTCCCACTCTCCTGGTAAATGA
Italic region: signal peptide coding sequence
Bold-faced region: variable chain coding sequence (SEQ ID NO: 4)
Bold-faced and underlined regions: CDR coding sequences
Regular font regions: constant region coding sequences
Underlined region: hinge region coding sequence Light chain amino acid sequence:
(SEQ ID NO: 5)

*MKLPVRLLVLMFWIPASRS*DIVMTQTPLSLPVSLGDQAS

ISC<u>RSSQSLVHSNGKTYLH</u>WYLQKPGQSPKLLIY<u>KVSNR</u>

<u>FS</u>GVPDRFSGSGSGTDFTLKISRVEAEDLGVYFC<u>SQSTH</u>

<u>VP</u><u>WTFGGGTKLEIKR</u>ADAAPTVSIFPPSSEQLTSGGASV

VCFLNNFYPKDINVKWKIDGSERQNGVLNSWTDQDSKDS

TYSMSSTLTLTKDEYERHNSYTCEATHKTSTSPIVKSFN

RNEC
Italic region: signal peptide
Bold-faced region: variable chain (SEQ ID NO: 6)
Bold-faced and underlined regions: CDRs
Regular font region: constant region
Underlined region: joining segment Light chain nucleotide sequence:
(SEQ ID NO: 7)

*ATGAAGTTGCCTGTTAGGCTGTTGGTGCTGATGTTCTGGATTCCTGCTTCCAGGAGT*GATATTGTGATGACCCAAACT

CCACTCTCCCTGCCTGTCAGTCTTGGAGATCAAGCCTCCATCTCTTGC<u>AGATCTAGTCAGAGCCTTGTACACAGTAAT</u>

<u>GGAAAAACCTATTTACATT</u>GGTACCTGCAGAAGCCAGGCCAGTCTCCTAAGCTCCTGATCTAC<u>AAAGTTTCCAACCGA</u>

TTTTCTGGGGTCCCAGACAGGTTCAGTGGCAGTGGATCAGGGACAGATTTCACACTCAAGATCAGCAGAGTGGAGGCT

GAGGATCTGGGAGTTTATTTCTGCTCTCAAAGCACACATGTTCCG*TGGACGTTCGGTGGAGGCACCAAGCTGGAAATC*

AAACGGGCTGATGCTGCACCAACTGTATCCATCTTCCCACCATCCAGTGAGCAGTTAACATCTGGAGGTGCCTCAGTC

GTGTGCTTCTTGAACAACTTCTACCCCAAAGACATCAATGTCAAGTGGAAGATTGATGGCAGTGAACGACAAAATGGC

GTCCTGAACAGTTGGACTGATCAGGACAGCAAAGACAGCACCTACAGCATGAGCAGCACCCTCACGTTGACCAAGGAC

GAGTATGAACGACATAACAGCTATACCTGTGAGGCCACTCACAAGACATCAACTTCACCCATTGTCAAGAGCTTCAAC

AGGAATGAGTGTTAG
Italic region: signal peptide coding sequence
Bold-faced region: variable chain coding sequence (SEQ ID NO: 8)
Bold-faced and underlined regions: CDR coding sequences
Regular font region: constant region coding sequence
Underlined region: joining segment coding sequence Antibody 1BB1 can be produced by a conventional method, i.e., produced from a hybridoma cell line as described in Hsing et al., *Cytokine* 44:221-228; 2008, synthesized chemically, or expressed via recombinant technology.

A functional variant of 1BB1 contains a $V_H$ at least 75% (80%, 85%, 90%, or 95%) identical to that of 1BB1 (SEQ ID NO:2) and a $V_L$ at least 75% (80%, 85%, 90%, or 95%) identical to that of 1BB1 (SEQ ID NO:6). As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See ncbi.nlm.nih.gov.

A functional variant of 1BB1 (e.g., a humanized antibody) can be generated by introducing mutations in a frame region (FR) of either the $V_H$ or $V_L$ of 1BB1 and keep intact their CDRs, particularly the specific-determining residues in these regions. It is well known that CDRs of an antibody determine its specificity. Accordingly, mutations in FRs normally would not affect antibody specificity. The CDRs and FRs of an antibody can be determined based on the amino acid sequences of its $V_H$ and $V_L$. See bioinf.org.uk/abs. The binding-specificity of the functional equivalents described herein can be examined using methods known in the art, e.g., ELISA or Western-blot analysis.

Alternatively, a functional variant of 1BB1 is a genetically engineered antibody containing the same $V_H$ and $V_L$ as 1BB1. Such a variant (e.g., a chimeric antibody or a single-chain antibody) can be prepared following methods described above.

The anti-20 antibody to be co-used with an anti-IL-19 antibody for treating breast cancer can be monoclonal antibody 7E, which neutralizes IL-20 activity, or a functional variant thereof, mAb7E is produced by the hybridoma cell line deposited at the American Type Culture Collection, 10801 Univer city Boulevard, Manassas, Va. 20110-2209, U.S.A. and assigned a deposit number PTA-8687. See U.S. Pat. No. 7,435,800 and US 20090048432. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. The amino acid sequences/cDNA sequences of the heavy and light chains of mAb7E are shown below.

```
Nucleotide sequence (SEQ ID NO: 9) and amino acid sequence
(SEQ ID NO: 10) of mAb 7E heavy chain
atg tac ttg gga ctg aac tat gta ttc ata gtt ttt ctc tta aat
 M   Y   L   G   L   N   Y   V   F   I   V   F   L   L   N      15 ggt gtc cag agt gaa ttg aag ctt gag gag tct gga gga ggc ttg
 G   V   Q   S   E   L   K   L   E   E   S   G   G   G   L      30 gtg cag cct gga gga tcc atg aaa ctc tct tgt gct gcc tct gga
 V   Q   P   G   G   S   M   K   L   S   C   A   A   S   G      45 ttc act ttt agt gac gcc tgg atg gac tgg gtc cgc cag tct cca
 F   T   F   S   D   A   W   M   D   W   V   R   Q   S   P      60 gag aag ggg ctt gag tgg att gct gaa att aga agc aaa gct aat
 E   K   G   L   E   W   I   A   E   I   R   S   K   A   N      75 aat tat gca aca tac ttt gct gag tct gtg aaa ggg agg ttc acc
 N   Y   A   T   Y   F   A   E   S   V   K   G   R   F   T      90 atc tca aga gat gat tcc aaa agt ggt gtc tac ctg caa atg aac
 I   S   R   D   D   S   K   S   G   V   Y   L   Q   M   N     105
```

```
aac tta aga gct gag gac act ggc att tat ttc tgt acc aag tta
 N   L   R   A   E   D   T   G   I   Y   F   C   T   K   L   120 tca cta cgt tac tgg ttc ttc gat gtc tgg ggc gca ggg acc acg
 S   L   R   Y   W   F   F   D   V   W   G   A   G   T   T   135 gtc acc gtc tcc tca gcc aaa acg aca ccc cca tct gtc tat cca
 V   T   V   S   S   A   K   T   T   P   P   S   V   Y   P   150 ctg gcc cct gga tct gct gcc caa act aac tcc atg gtg acc ctg
 L   A   P   G   S   A   A   Q   T   N   S   M   V   T   L   165 gga tgc ctg gtc aag ggc tat ttc cct gag cca gtg aca gtg acc
 G   C   L   V   K   G   Y   F   P   E   P   V   T   V   T   180 tgg aac tct gga tcc ctg tcc agc ggt gtg cac acc ttc cca gct
 W   N   S   G   S   L   S   S   G   V   H   T   F   P   A   195 gtc ctg cag tct gac ctc tac act ctg agc agc tca gtg act gtc
 V   L   Q   S   D   L   Y   T   L   S   S   S   V   T   V   210 ccc tcc agc acc tgg ccc agc gag acc gtc acc tgc aac gtt gcc
 P   S   S   T   W   P   S   E   T   V   T   C   N   V   A   225 cac ccg gcc agc agc acc aag gtg gac aag aaa att gtg ccc agg
 H   P   A   S   S   T   K   V   D   K   K   I   V   P   R   240 gat tgt ggt tgt aag cct tgc ata tgt aca gtc cca gaa gta tca
 D   C   G   C   K   P   C   I   C   T   V   P   E   V   S   255 tct gtc ttc atc ttc ccc cca aag ccc aag gat gtg ctc acc att
 S   V   F   I   F   P   P   K   P   K   D   V   L   T   I   270 act ctg act cct aag gtc acg tgt gtt gtg gta gac atc agc aag
 T   L   T   P   K   V   T   C   V   V   V   D   I   S   K   285 gat gat ccc gag gtc cag ttc agc tgg ttt gta gat gat gtg gag
 D   D   P   E   V   Q   F   S   W   F   V   D   D   V   E   300 gtg cac aca gct cag acg caa ccc cgg gag gag cag ttc aac agc
 V   H   T   A   Q   T   Q   P   R   E   E   Q   F   N   S   315 act ttc cgc tca gtc agt gaa ctt ccc atc atg cac cag gac tgg
 T   F   R   S   V   S   E   L   P   I   M   H   Q   D   W   330 ctc aat ggc aag gag ttc aaa tgc agg gtc aac agt gca gct ttc
 L   N   G   K   E   F   K   C   R   V   N   S   A   A   F   345 cct gcc ccc atc gag aaa acc atc tcc aaa acc aaa ggc aga ccg
 P   A   P   I   E   K   T   I   S   K   T   K   G   R   P   360 aag gct cca cag gtg tac acc att cca cct ccc aag gag cag atg
 K   A   P   Q   V   Y   T   I   P   P   P   K   E   Q   M   375 gcc aag gat aaa gtc agt ctg acc tgc atg ata aca gac ttc ttc
 A   K   D   K   V   S   L   T   C   M   I   T   D   F   F   390 cct gaa gac att act gtg gag tgg cag tgg aat ggg cag cca gcg
 P   E   D   I   T   V   E   W   Q   W   N   G   Q   P   A   405 gag aac tac aag aac act cag ccc atc atg gac aca gat ggc tct
 E   N   Y   K   N   T   Q   P   I   M   D   T   D   G   S   420 tac ttc gtc tac agc aag ctc aat gtg cag aag agc aac tgg gag
 Y   F   V   Y   S   K   L   N   V   Q   K   S   N   W   E   435 gca gga aat act ttc acc tgc tct gtg tta cat gag ggc ctg cac
 A   G   N   T   F   T   C   S   V   L   H   E   G   L   H   450 aac cac cat act gag aag agc ctc tcc cac tct cct ggt aaa TGA
 N   H   H   T   E   K   S   L   S   H   S   P   G   K   -   464
```
The bold-faced region refers to the V$_H$ of mAb 7E heavy chain
(DNA sequence SEQ ID NO: 11; protein sequence SEQ ID NO: 12)

Nucleotide sequence (SEQ ID NO: 13) and amino acid sequence
(SEQ ID NO: 14) of mAb 7E light chain
```
atg atg agt cct gcc cag ttc ctg ttt ctg tta gtg ctc tgg att
 M   M   S   P   A   Q   F   L   F   L   L   V   L   W   I    15 cgg gaa acc aac ggt gat ttt gtg atg acc cag act cca ctc act
 R   E   T   N   G   D   F   V   M   T   Q   T   P   L   T    30
```

```
ttg tcg gtt acc att gga caa cca gcc tcc atc tct tgc aag tca
 L   S   V   T   I   G   Q   P   A   S   I   S   C   K   S    45 agt cag agc ctc ttg gat agt gat gga aag aca tat ttg aat tgg
 S   Q   S   L   L   D   S   D   G   K   T   Y   L   N   W    60 ttg tta cag agg cca ggc cag tct cca aag cac ctc atc tat ctg
 L   L   Q   R   P   G   Q   S   P   K   H   L   I   Y   L    75 gtg tct aaa ctg gac tct gga gtc cct gac agg ttc act ggc agt
 V   S   K   L   D   S   G   V   P   D   R   F   T   G   S    90 gga tca ggg acc gat ttc aca ctg aga atc agc aga gtg gag gct
 G   S   G   T   D   F   T   L   R   I   S   R   V   E   A   105 gag gat ttg gga gtt tat tat tgc tgg caa agt aca cat ttt ccg
 E   D   L   G   V   Y   Y   C   W   Q   S   T   H   F   P   120 tgg acg ttc ggt gga ggc acc aag ctg gaa atc aaa cgg gct gat
 W   T   F   G   G   G   T   K   L   E   I   K   R   A   D   135 gct gca cca act gta tcc atc ttc cca cca tcc agt gag cag tta
 A   A   P   T   V   S   I   F   P   P   S   S   E   Q   L   150 aca tct gga ggt gcc tca gtc gtg tgc ttc ttg aac aac ttc tac
 T   S   G   G   A   S   V   V   C   F   L   N   N   F   Y   175 aag tgg aag att gat ggc agt gaa cga caa aat ggc gtc ctg aac
 P   K   D   I   N   V   K   W   K   I   D   G   S   E   R   180 agt tgg act gat cag ccc aaa gac atc aat gtc gac agc aaa gac
 Q   N   G   V   L   N   S   W   T   D   Q   D   S   K   D   195 agc acc tac agc atg agc agc acc ctc acg ttg acc aag gac gag
 S   T   Y   S   M   S   S   T   L   T   L   T   K   D   E   210 tat gaa cga cat aac agc tat acc tgt gag gcc act cac aag aca
 Y   E   R   H   N   S   Y   T   C   E   A   T   H   K   T   225 tca act tca ccc att gtc aag agc ttc aac agg aat gag tgt tag
 S   T   S   P   I   V   K   S   F   N   R   N   E   C   —   239
```
The bold-faced region refers to the $V_L$ of mAb 7E light chain (DNA sequence SEQ ID NO: 15; protein sequence SEQ ID NO: 16).

When two antibodies are used in treating breast cancer, they can form a bi-specific complex (i.e., bi-specific antibody), which contains two antigen-binding domains (i.e., two heavy-light chain pairs), one specific to IL-19 and the other specific to IL-20. Such a bi-specific antibody can be prepared via conventional methods.

When used for treating breast cancer, any of the anti-IL-19 antibodies described herein can be mixed with a pharmaceutically acceptable carrier, either alone or in combination with an anti-IL-20 or anti-IL-20R1 antibody, to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

The above-described pharmaceutical composition can be administered via a conventional route, e.g., orally, parenterally, by inhalation spray, topically, rectally, nasally, buccally, vaginally or via an implanted reservoir, to treat breast cancer. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In addition, the pharmaceutical composition described above can be administered to the subject via injectable depot routes of administration such as using 1-, 3-, or 6-month depot injectable or biodegradable materials and methods.

Without further elaboration, it is believed that one skilled in the art can, based on the above description, utilize the present invention to its fullest extent. The following specific embodiments are, therefore, to be construed as merely illus-

Example 1

Anti-IL-19 Antibody 1BB1 Inhibited Proliferation of Breast Cancer Cells

Human MCF-7 and mouse 4T1 breast cancer cells were cultured in a growth medium in the absence of fetal calf serum for 16 h. $2\times10^5$ MCF-7 or 4T1 cells were then seeded and cultured in the medium supplemented with 2% FBS for 24 hours in the presence PBS, human IL-19 (200 or 400 μg/mL for MCF-7 cells), mouse IL-19 (200 or 400 μg/mL for 4T1 cells), antibody 1BB1 (8 μg/ml), or a combination of IL-19 and antibody 1BB1 (1:10). The cells were then incubated in a solution containing 3[4,5-Dimethylthiazol-2-yl]-2,5-diphenyltetrazolium bromide (MTT) (1 mg/ml; Sigma-Aldrich) for 3 hours. Afterwards, dimethyl sulfoxide (DMSO) was added to the cultures and absorbance at 500 nm was determined. FBS (10%) (Sigma-Aldrich) was used as the positive control.

Figure 1:
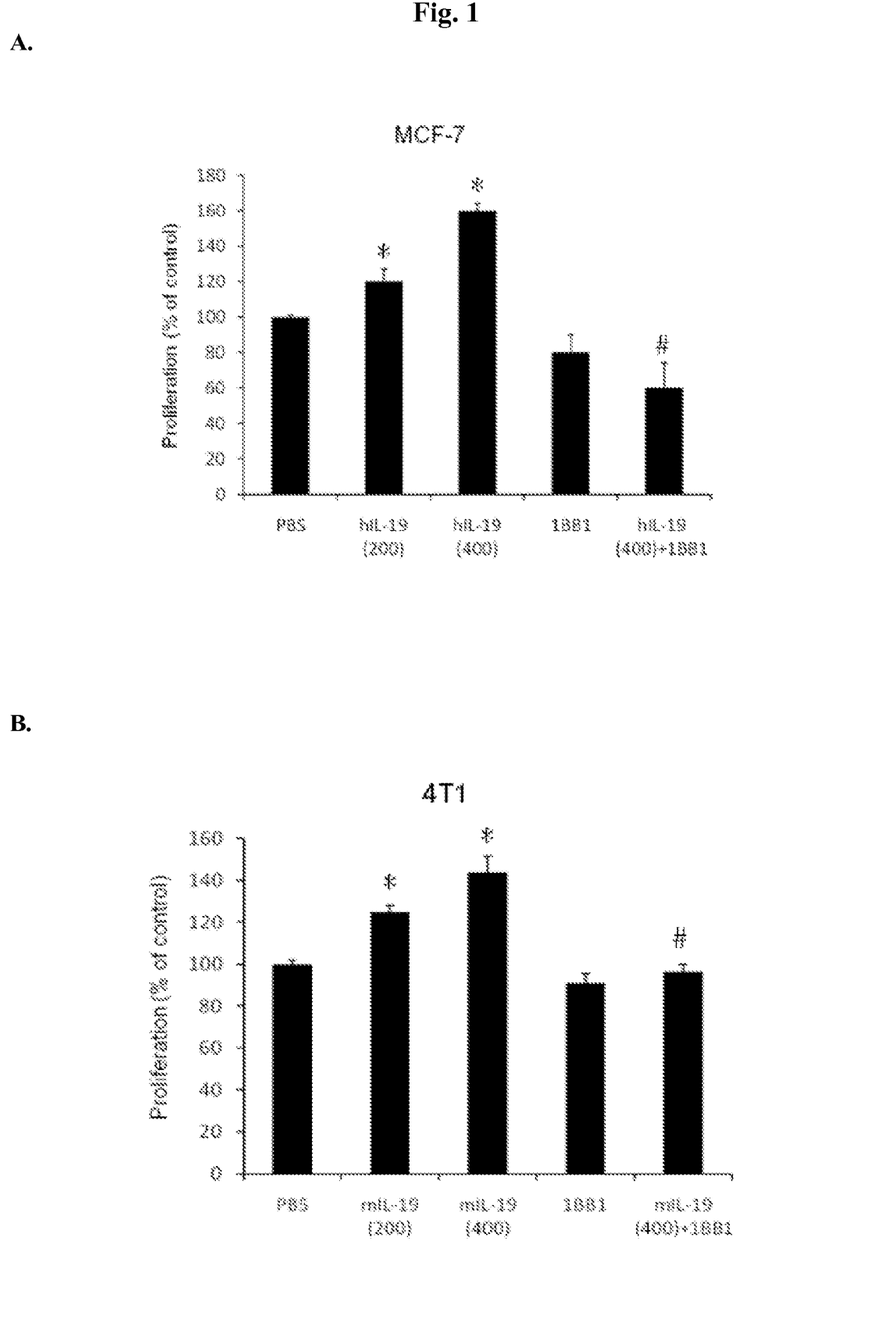
FIG. 1 is a chart showing the effect of anti-IL-19 antibody 1BB1 in suppressing breast cancer cell proliferation. Panel A: suppression of MCF-7 cancer cell proliferation by antibody 1BB1. Panel B: suppression of 4T1 cancer cell proliferation by antibody 1BB1. *$P<0.05$ as compared to cells treated with PBS control; #$P<0.05$ as compared to cells treated with IL-19.

As shown in FIG. 1, human IL-19 and mouse IL-19 induced proliferation of MCF-7 cells and 4T1 cells, respectively, in a dose-dependent manner. Anti-IL-19 antibody 1BB1 successfully inhibited breast cancer cell proliferation.

Example 2

Treating Breast Cancer with Antibody 1BB1

The effect of anti-IL-19 antibody 1BB1 on the survival of mice bearing breast cancer was investigated as follows. Mouse breast cancer 4T1 cells were cultured under suitable conditions, collected, and re-suspended in PBS at a final concentration of $2\times10^5/100$ μL. The 4T1 cells ($2\times10^5/100$ μL) were injected directly into the left ventricle of 6-wk-old female BALB/c mice, anesthetized with pentobarbital (50 mg/kg body weight, i.p.), using an insulin syringe (29 gauge, BD Ultra-Fine; Becton Dickinson). The mice were then randomly assigned to 3 groups (n=6/group), each treated with vehicle (PBS), a control mouse antibody (mIgG, 10 mg/kg), or antibody 1BB1 (10 mg/kg) by i.p. injection three times in one week. Mice not injected with 4T1 cells were used as healthy controls. The survival rates of the three groups and the healthy controls were monitored on a daily basis until the end of the experiment.

Figure 2:
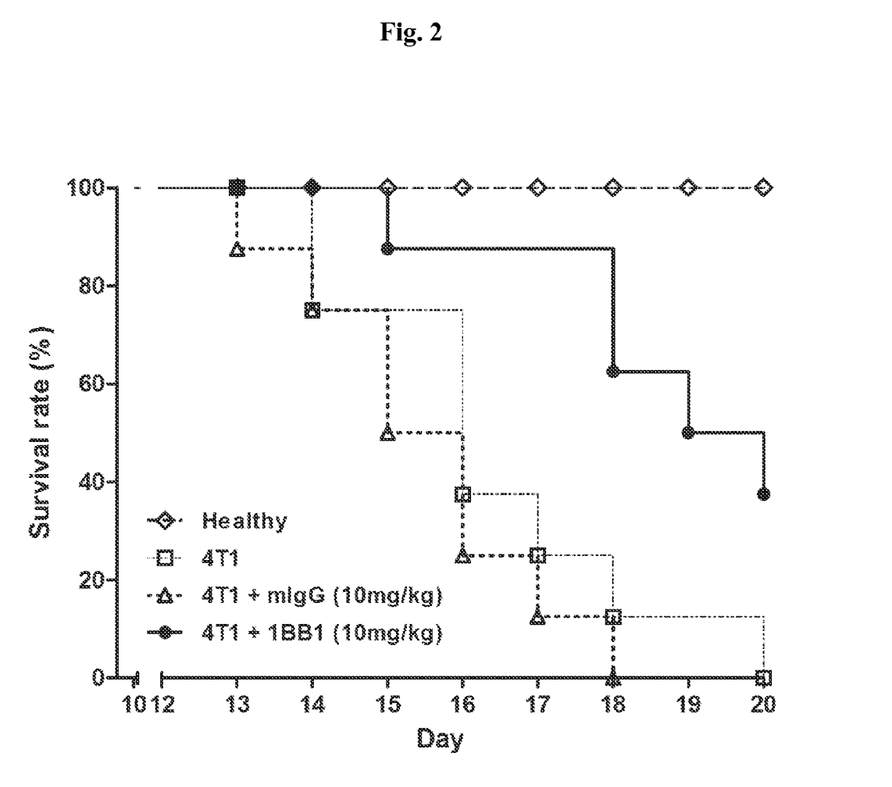
FIG. 2 is a diagram showing the effect of 1BB1 in prolonging survival of mice bearing breast cancer.

The results obtained from this study indicate that the survival rate of the group 3 mice, treated with antibody 1BB1, was much higher than that of the group 1 or group 2 mice, treating with PBS or mIgG, respectively. See FIG. 2.

Further, the effect of antibody 1BB1 on breast tumor growth was explored. Mouse cancer 4T1 cells ($2\times10^6$ cells) were injected into the mammary fat pads of BALB/c mice to allow tumor growth. The mice were then treated via subcutaneous injection with PBS as a blank control, antibody 1BB1 (15 mg/kg), or mouse control antibody mIgG (15 mg/kg), once every three days. Thirty day after the tumor cell injection, the mice were sacrificed and the tumors in them were collected and weighed.

Figure 3:
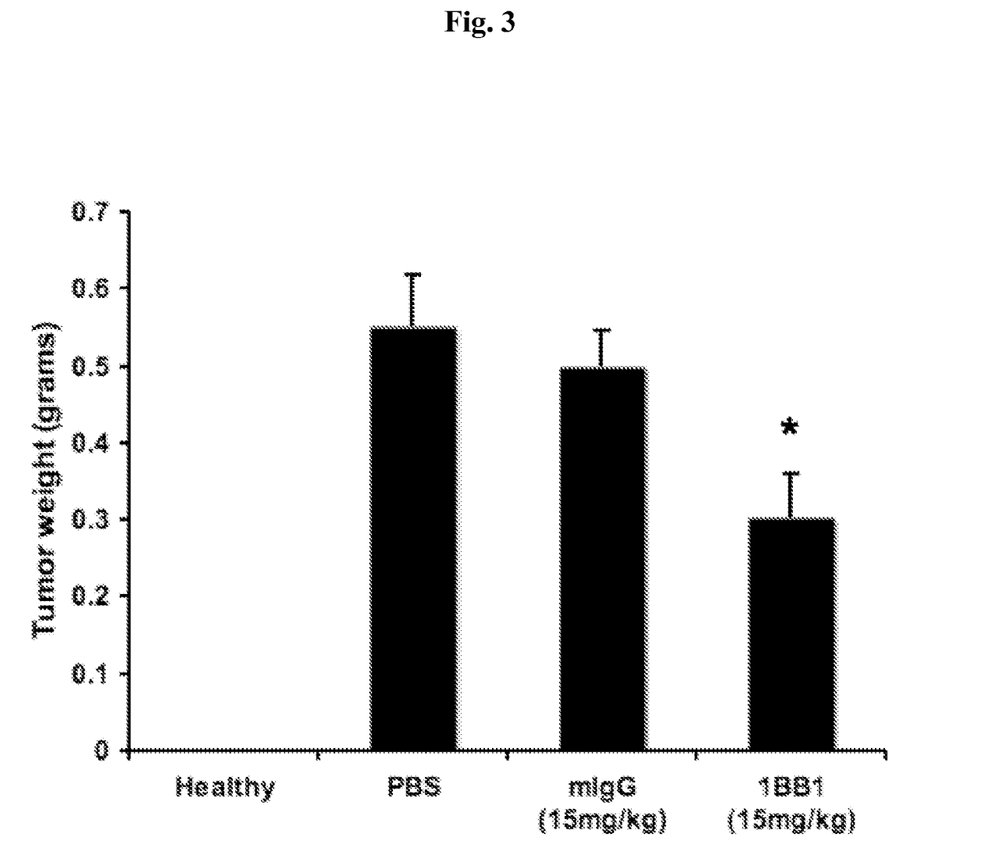
FIG. 3 is a chart showing the effect of antibody 1BB1 in suppressing breast tumor growth in mice.

As shown in FIG. 3, the weight of the tumors in 1BB1-treated mice was significantly lower than that in PBS-treated or mIgG-treated mice ($P<0.05$).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating breast cancer, comprising administering to a subject in need thereof an effective amount of an anti-IL-19 antibody.

2. The method of claim 1, wherein the anti-IL-19 antibody is a humanized antibody, a chimeric antibody, a single-chain antibody, a monoclonal antibody or an antigen-binding fragment thereof.

3. The method of claim 2, wherein the anti-IL-19 antibody contains a heavy chain variable region including all of the complementarity-determining regions in SEQ ID NO:2 and a light chain variable region including all of the complementarity-determining regions in SEQ ID NO:6.

4. The method of claim 3, wherein the anti-IL-19 antibody contains a heavy chain variable region including SEQ ID NO:2 and a light chain variable region including SEQ ID NO:6.

5. The method of claim 4, wherein the anti-IL-19 antibody is a chimeric antibody or a single-chain antibody.

6. The method of claim 4, wherein the anti-IL-19 antibody is monoclonal antibody 1BB1 or an antigen-binding fragment thereof.

7. The method of claim 1, wherein the subject is a human patient suffering from or at risk for breast cancer.

8. The method of claim 7, wherein the subject is a breast cancer patient suffering from cancer metastasis.

9. The method of claim 8, wherein the anti-IL-19 antibody is a humanized antibody, a chimeric antibody, a single-chain antibody, a monoclonal antibody or an antigen-binding fragment thereof.

10. The method of claim 8, wherein the anti-IL-19 antibody contains a heavy chain variable region including all of the complementarity-determining regions in SEQ ID NO:2 and a light chain variable region including all of the complementarity-determining regions in SEQ ID NO:6.

11. The method of claim 10, wherein the anti-IL-19 antibody contains a heavy chain variable region including SEQ ID NO:2 and a light chain variable region including SEQ ID NO:6.

12. The method of claim 11, wherein the anti-IL-19 antibody is a chimeric antibody or a single-chain antibody.

13. The method of claim 11, wherein the anti-IL-19 antibody is monoclonal antibody 1BB1 or an antigen-binding fragment thereof.

14. The method of claim 1, further comprising administering to the subject an effective amount of an anti-IL-20 antibody.

15. The method of claim 14, wherein the anti-IL-20 antibody is monoclonal antibody 7E, an antigen-binding fragment thereof, or a genetically engineered antibody thereof, which comprises the same complementarity-determining regions as monoclonal antibody 7E.

16. The method of claim 14, wherein the anti-IL-20 antibody forms a bi-specific complex with the anti-IL-19 antibody.

17. The method of claim 16, wherein both the anti-IL-19 antibody and the anti-IL-20 antibody are Fab fragments.

18. The method of claim 1, further comprising administering to the subject an effective amount of an anti-IL-20R1 antibody.

19. The method of claim 18, wherein the anti-IL-20R1 antibody is a monoclonal antibody, or an antigen-binding fragment thereof.

20. The method of claim 18, wherein the anti-IL-20R1 antibody forms a bi-specific complex with the anti-IL-19 antibody.

21. The method of claim 20, wherein both the anti-IL-19 antibody and the anti-IL-20R1 antibody are Fab fragments.

* * * * *